United States Patent [19]
Tarka, Jr. et al.

[11] Patent Number: 5,219,573
[45] Date of Patent: Jun. 15, 1993

[54] L-SUGAR LAXATIVES

[75] Inventors: Stanley M. Tarka, Jr., Hershey; Carol A. Shively, Mechanicsburg; Joan L. Apgar, Hummelstown; Kenneth L. Koch, Hershey, all of Pa.

[73] Assignee: Hershey Foods Corporation, Hershey, Pa.

[21] Appl. No.: 422,694

[22] Filed: Oct. 17, 1989

[51] Int. Cl.$^5$ .............................. A61K 31/70
[52] U.S. Cl. ..................... 424/439; 514/23; 514/892; 426/658; 536/1.11
[58] Field of Search ............... 536/1.1, 4.1; 514/892, 514/23; 424/439; 426/658

[56] References Cited

U.S. PATENT DOCUMENTS 4,470,975  9/1984  Berger et al. ..................... 536/4.1
4,859,488  8/1989  Kan et al. ......................... 536/1.1

FOREIGN PATENT DOCUMENTS 1238577  5/1983  Canada .

Primary Examiner—Thurman K. Page
Assistant Examiner—James M. Spear
Attorney, Agent, or Firm—Scully, Scott, Murphy & Presser

[57] ABSTRACT

The present invention relates to novel monosaccharide sweeteners which are capable of acting as laxatives when administered in dose-effective amounts. The present invention also contemplates monosaccharides with laxative properties which have a natural carbohydrate structure. More specifically, the present invention contemplates monosaccharide substances capable of producing laxative effects in humans and having the advantages of being only minimally absorbed from the intestine; and having osmotic laxative effects on the small bowel and colon. The present invention allows for improved laxative formulations with increased palatability and better dosing for all age groups. The present invention can be used to induce mild laxation six to ten hours after ingestion.

9 Claims, 11 Drawing Sheets

FIG. 8
EFFECT OF L-GLUCOSE ON EPISODES OF DIARRHEA

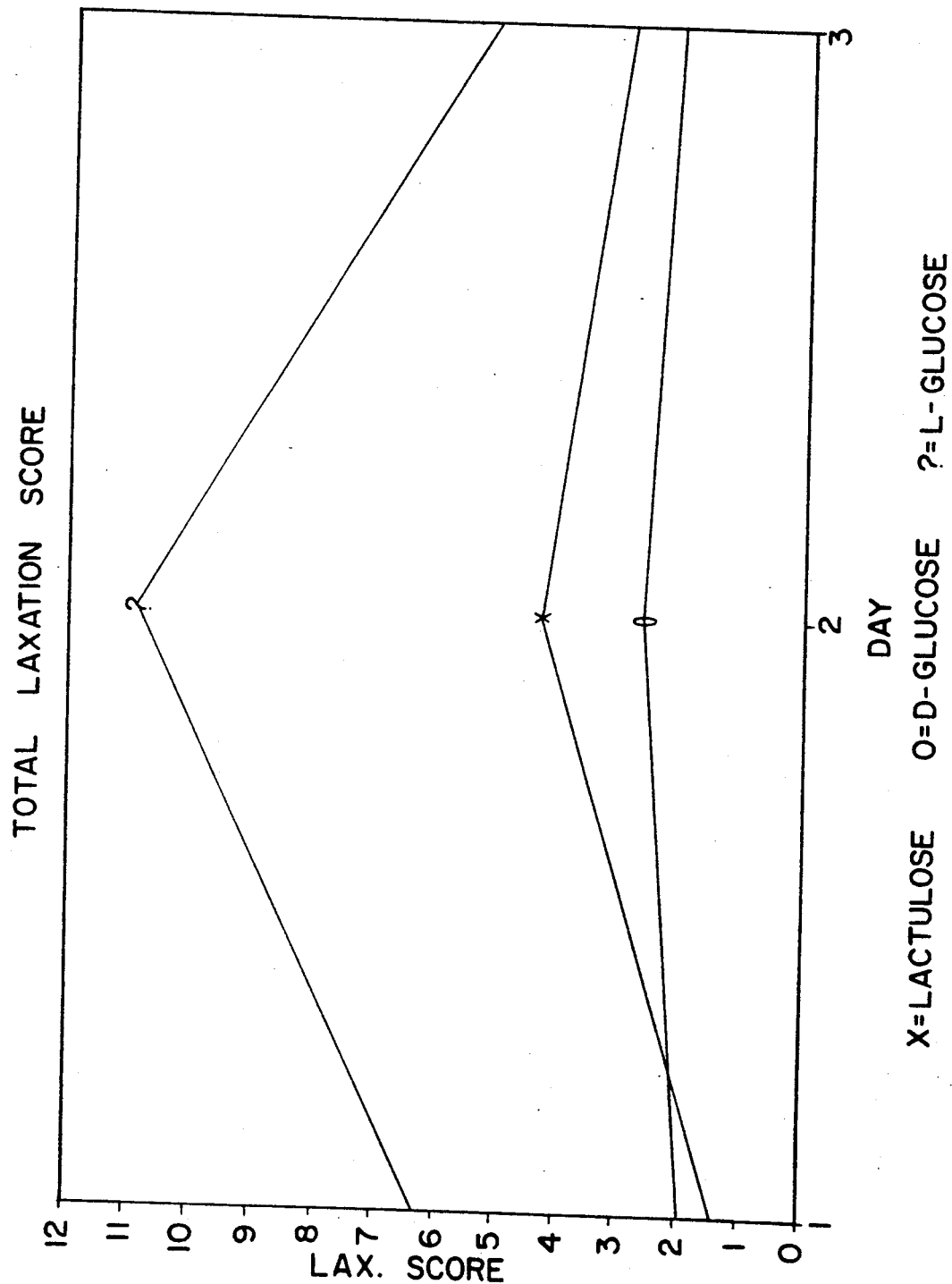

L-SUGAR LAXATIVES

FIELD OF THE INVENTION

The present invention relates to a novel monosaccharide sweetener which is capable of acting as a laxative when administered in dose-effective amounts. The present invention also contemplates monosaccharides with laxative properties which have a natural carbohydrate structure.

More specifically, the present invention contemplates a monosaccharide capable of producing laxative effects in humans and having the advantages of being only minimally absorbed from the intestine; and having osmotic laxative and stool softening effects on the small bowel and colon. The present invention allows for improved laxative formulations with increased palatability and better dosing for all age groups. The present invention can be used to induce mild laxation six to ten hours after ingestion.

BACKGROUND OF THE INVENTION

The treatment of constipation problems has been a concern of physicians for years. Constipation has been defined as less than one bowel movement per week. Other components of constipation include difficulties with defecation and stool hardness.

Alternating constipation and diarrhea or painful constipation are symptoms of one of the most common ailments in medicine and in the practice of gastroenterology—the irritable bowel syndrome. In this syndrome, the constipation is believed to be due to altered colonic motility, but neural and hormonal abnormalities and psychosocial stresses may also contribute to the syndrome.

Other common and accepted causes of constipation include: endocrine disorders such as diabetes, hypothyroidism, and hyper/hypocalcemia; spinal and head injuries which disrupt the parasympathetic nerve circuits to the colon; anal canal or rectal contraction abnormalities; pelvic floor abnormalities preventing proper angulation for defecation; neuromuscular disorders such as intestinal pseudo-obstruction and colonic inertia. Encopresis is a constipation problem in pediatrics. Constipation also is a major concern of the elderly populations who are sedentary, who may have inadequate diets, and who take numerous medications which may interfere with normal bowel function.

Treatment of common and typical constipation takes the form of time honored remedies ranging from mineral oil to castor oil to fiber and bran. Treatments have been empirical because the mechanisms and causes of constipation are still poorly understood.

The four major classes of laxatives which can be used in the treatment of constipation are: osmotic laxatives, bulking agents, stimulant agents, and stool softeners. The osmotic laxatives are saline cathartics and include compounds such as lactulose, golytely or colyte, mannitol or mannose, or magnesium citrate. Lactulose is available as a component of the commercial product Chronulac, a non-absorbable synthetic disaccharide (lactulose, 10 g; plus galactose, 2.2 g; and lactose 1.2 g per dose).

Chronulac is poorly absorbed and reaches the colon virtually unchanged where it is broken down by colonic bacteria to volatile fatty acids. Production of these fatty acids results in a slight acidification in the intestine and results in increased osmotic pressure. In turn, this causes an increase in stool water content and stool softening.

Chronulac often takes 24-28 hours to work. Three percent of a dose generally appears in the urine. A major side effect is excessive gas. Chronulac is available by prescription and only in a syrup form. Usual doses are 30-40 gm three to four times a day.

Golytely and colyte are balanced electrolyte solutions plus polyethylene glycol. Their primary use is to prepare the colon for barium enema studies and for colonoscopy. Polyethylene glycol is not absorbed and causes an osmotic diarrhea. The electrolytes are absorbed to maintain the body's fluid balance during intense laxation. These solutions are advantageous in that the colon is thoroughly cleansed and no explosive gases are produced, which would become problematic if polypectomy is planned. The major disadvantage is that patients must drink 4 liters of the solution in 3-4 hours and many patients are unable to do so or find this very unpleasant because of bloating and nausea.

Mannitol or mannose agents are poorly absorbed carbohydrates, but are seldom used because enough carbohydrate does get absorbed to present an osmotic load to the kidney resulting in diuresis. Gas formation makes polypectomy dangerous. Magnesium citrate is a lemon-lime flavored liquid which is an effective laxative when more vigorous laxation is needed.

Bulking agents include fiber products (such as Metamucil) and Perdiem. Increases in stool weight, stimulation of colonic motility and increases in stool water have been described after using these agents. Bulking agents are the preferred products used by most gastroenterologists for common constipation or for the constipation associated with the irritable bowel syndrome. However, almost all patients complain of the mucilagenous consistency of metamucil-type preparations. Many new products have been developed to cover-up the fiber nature of these preparations but none have been particularly successful. The product is also unsatisfactory for patients with esophageal or gastric motility disorders. These patients have trouble swallowing and experience bloating, distention and increased gas after ingestion.

Perdiem is an effective product since it provides the bran psyllium in a well-tolerated granular form. However, administration of Perdiem is unusual in that the crystals (one teaspoon) are supposed to be swallowed dry. Perdiem can also be used with senna. The senna adds a laxative to the fiber for the patient with more severe constipation.

Stimulant agents include phenolphthalein-containing laxatives, castor oil and Dulcolax. Phenolphthalein-containing laxatives, e.g., Exlax/Correctol, are the common over-the-counter laxatives that many people take for mild constipation. Gastroenterologists and knowledgable physicians warn against these products, however, because they are relatively habit forming. It is noted that while the causes of constipation are many, in most people the cause is unknown. Because constipation is a recurring problem, most people take phenolphthalein products recurrently.

Chronic use of phenolphthalein may result in "cathartic colon", a well-accepted entity hallmarked by a dilated, weak colon which is unable to contract normally and thus unable to empty stool, resulting in a vicious cycle. Some studies have shown that in laxative abusers the colon loses its neural control because of damage to the myenteric plexus, possibly due to phenolphthalein effects. Approximately 15% of the phenolphthalein is absorbed, and can cause gripping pain or intestinal cramps.

Castor oil is a well-known stimulant cathartic. The active ingredient in castor oil is ricinoleic acid. Castor oil is a very potent cathartic which often causes abdominal cramping and severe diarrhea. Most patients complain about the taste and the abdominal pain induced by castor oil. Dulcolax (bisacodyl) is a very effective stimulant laxative which is available in tablet or suppository form. Minimal amounts of bisacodyl are absorbed.

Stool softeners, also known as emollients are epitomized by Colace (dioctyl sodium sulfosuccinate), an agent which may be purchased over the counter to soften stools. Most gastroenterologists do not prescribe these compounds because they are relatively ineffective, particularly in the patients with more than mild constipation. The bulking agents are generally preferred to the softening agents.

Mineral oil is also in the group of softeners but has toxicities such as interference with absorption of essential fatty acids and the well-known possibility of aspiration and lipid pneumonitis. Thus most physicians do not prescribe mineral oil.

The present invention contemplates the administration of monosaccharides, and in particular, L-sugars, as laxatives with considerable advantages relative to the previously discussed classes of laxatives, all of which have various undesirable side effects as described above. Specifically, L-sugars are sweet tasting, vary in caloric content, and can readily be combined with other foodstuffs. The first scientifically designed study of the sweetness of L-sugars appears to be that of R. S. Shallenberger, T. E. Acree and C. Y. Lee, *Nature* 221: 555 (1969), who compared the relative sweetness of the D- and L-enantiomorphs of several sugars, including L-glucose, L-mannose, and L-galactose. Although differences between the enantiomers were observed, their results showed that the sweetness of the D- and L-enantiomers were comparable. Levin in U.S. Pat. No. 4,262,032 suggested employing L-sugars in sweetened edible formulations where the sweetener is non-calorific and less susceptible to spoilage through growth of microorganisms. This reference implied that none of the L-sugars would be metabolized by humans, and also that none will be physiologically or toxicologically detrimental without presenting data which speak to either point. L-sugars have several unique attributes not expected in view of the prior art. In the present invention, we have discovered that, while L-sugars are generally poorly metabolized, there are distinct differences in their excretion patterns and metabolic fates.

L-sugars can act as osmotic laxatives similar to lactulose, but the L-sugar can be formulated and administered in a more convenient and palatable form, such as a candy bar. Lactulose, for example, is available only as a liquid. The L-sugar produces less gas than lactulose, but can produce a lactulose-like effect The L-sugar would be considered "more natural" than lactulose and the onset of action more rapid. L-sugars are poorly absorbed in the human body, and therefore, have an advantage over mannitol, mannose and magnesium citrate in that there is little or no diuretic effect as found when using mannose or mannitol and no danger of magnesium exposure from use of magnesium citrate.

Barium enema prep kits use Dulcolax (bisacodyl) and enemas or the Colyte-type formulas to cleanse the bowel before barium X-rays. An appropriate larger dose of L-glucose may be capable of producing a "cleansing" of the bowel. The convenience and palatability of L-sugars would make them superior to bisacodyl and more palatable than drinking four liters of a high salt liquid over the course of 3–4 hours, e.g., Colyte. In circumstances where gas formation was a minor problem with an L-sugar, then a combination of L-sugar and a smaller (1–2 liter) volume of the polyethylene glycol solution may be advantageous for colon cleansing before X-ray studies, surgery and colonoscopy.

L-sugars have several advantages over the bulking agents currently in use. They can be prepared in a more palatable foodstuff than such products as Perdiem, with its peculiar granular consistency, and Metamucil, with its mucilagenous consistency. L-sugars also would have increased effectiveness and convenience (e.g., as a candy bar) over the prior-utilized products.

In using L-sugars rather than a stimulant agent, patients would avoid the potential harmful effects of recurrent exposure to phenolphthalein. L-sugars allow for more palatable forms of the laxative created in comparison with Exlax and castor oil, and avoids the cramping associated with castor oil and bisacodyl.

L-sugars are more advantageous than the stool softeners currently in use in that they have no sodium or calcium content than, e.g. the Colace and Surfak preparations, respectively.

SUMMARY OF THE INVENTION

Accordingly, one object of the present invention is to provide an improved method for treatment of constipation and constipation-related illnesses.

Another object of this invention is to provide an improved method of administering laxative treatment for constipation-related illnesses.

Still another object of this invention is to provide L-sugars which exhibit no short term adverse effects and which cause no long term detrimental physiological, toxicological, or genetic effect in the treatment of constipation and constipation-related illnesses.

A further object of this invention is to provide an L-sugar which has similar bulking properties to those of sucrose and dextrose, has the same mouth feel in various foods as when they are formulated with sucrose or other sugars and is capable of being readily crystallizable for easy processing, for the treatment of constipation and constipation-related illnesses.

Another object of this invention is to provide L-glucose administered in an effective and palatable laxative formulation for the treatment of constipation and constipation-related illnesses.

A still further object of this invention is to provide a new method which eliminates the disadvantages associated with conventional treatments of constipation and constipation-related illnesses.

These and other objects of the present invention are achieved by a protocol which permits a therapeutic range of an L-sugar to be administered once or twice daily as a laxative formulation.

BRIEF DESCRIPTION OF THE DRAWINGS

FIG. 8 is a graphical representation of the effect of L-glucose on episodes of diarrhea in human subjects over a period of hours.

FIG. 11 is a graphical representation of the effect of L-glucose, lactulose, and D-glucose on laxation in human subjects.

DETAILED DESCRIPTION OF THE INVENTION

Figure 1:
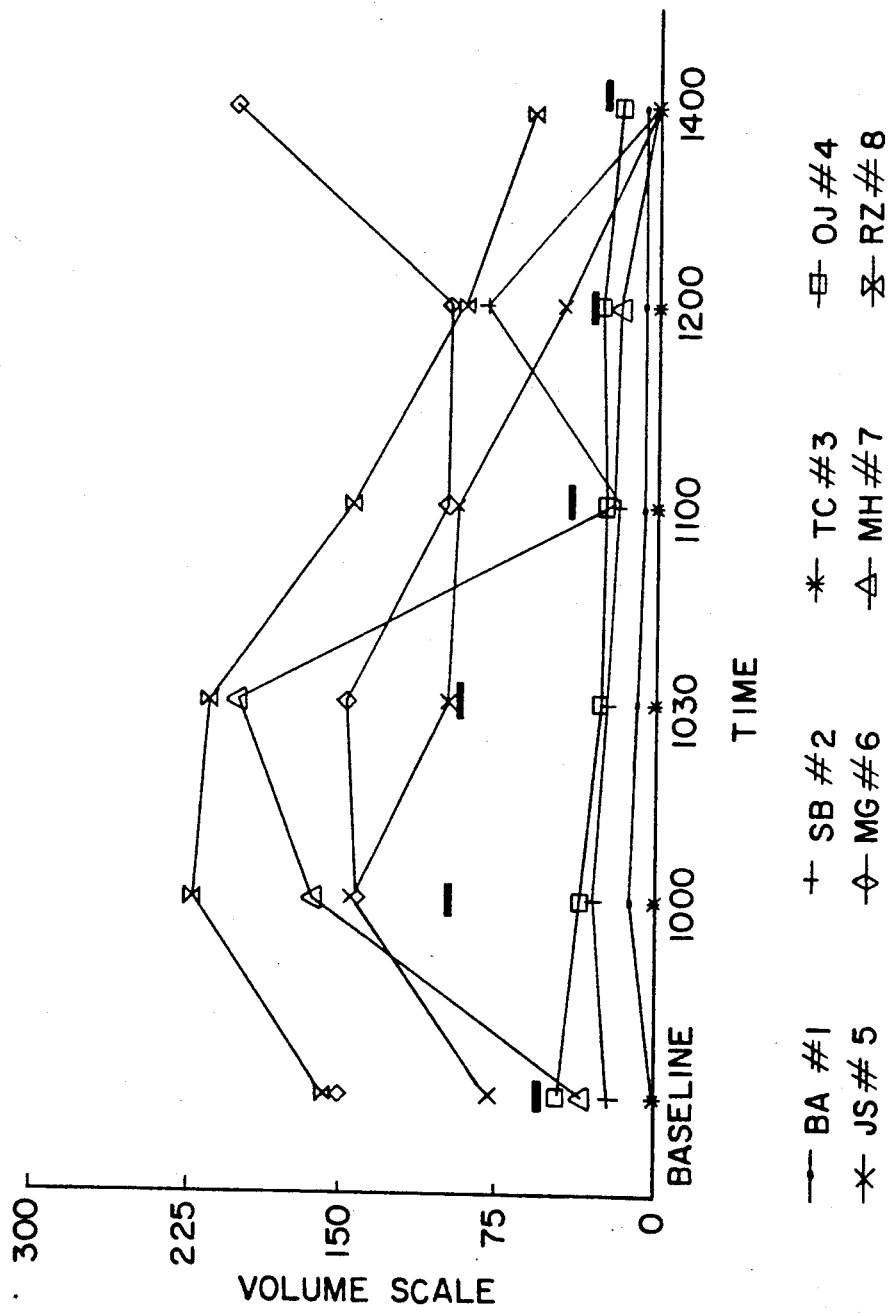
FIG. 1 is a graphical representation of the effect of L-glucose on the perception of gastric volume in human subjects.

The present invention contemplates a method of treating constipation and constipation-related illnesses. This method is achieved by employing a therapeutic range of a monosaccharide L-sugar in a laxative formulation. In accordance with the present invention, L-sugars have been found to be capable of providing mild to moderate laxation at lower doses for mild to moderate constipation problems through a putative osmotic mechanism. At higher doses L-sugars can provide cathartic effects needed to treat severe constipation or to cleanse the bowel for radiographic studies, surgical or endoscopic procedures. L-sugars uniquely possesses the characteristics which make them effective laxative agents relative to previously described osmotic laxatives, bulking agents, stimulant agents and stool softeners.

The L-sugars such as L-fructose, L-mannose, L-sorbose, L-gulose, and preferably, L-glucose are L-sugar sweeteners which are capable of causing laxative effects and/or soft stools (defined as the ability to initiate bowel movement) when ingested in amounts corresponding to a reasonable daily ingestion of a sweetener.

In a preferred embodiment L-glucose is employed as a laxative agent of choice. L-glucose is approximately as sweet as sucrose with no other objectionable taste or mouth feel. L-glucose is a bulking sweetener and can be substituted for sucrose and dextrose in a wide variety of food formulations such as candy, cakes, chewing gum, breathmints, pharmaceutical compositions, liquids, solids, suppositories, alone and in combination with various other sugars, syrups, foodstuffs, confections, baking goods, and flavorings, without necessitating any large changes in recipe L-glucose is metabolized in humans to a small extent (Table II). The sweetener is excreted unconverted in the urine and feces. The reason for this is that since L-glucose is of comparable sweetness to sucrose rather large amounts may be ingested in the normal diet. L-glucose can also be excreted in the feces, resulting in high osmotic pressure in the large intestine accompanying the accumulation of water soluble material which in turn would result in excessive water transport into the intestines, leading to laxative effects, e.g. loose or soft stools. L-glucose is also not significantly metabolized by intestinal flora. If there were significant metabolism by the body, flatulence could accompany its use, and the metabolic products in turn might be metabolized or assimilated by humans. L-glucose does not have detrimental physiological, toxicological, or genetic effects. L-glucose also undergoes the browning reaction to develop appropriate flavors when heated or baked. L-glucose is readily crystallized, since crystallinity often is needed to impart the correct mouth feel to a given foodstuff.

In light of their carbohydrate structures, we have discovered a number of unexpected and surprising attributes of L-sugars. In particular, L-glucose as employed in a laxative form exhibits minimal absorption from the intestine, has a unique action on the small bowel and colon as an osmotic laxative, acts as a mild laxative, has the capability for use in a variety of laxatives from softeners to cathartics, can be used in improved laxative formulations with increased palatability and better dosing for all age groups (e.g., infants, children, adolescents, adults, the elderly), and promotes rapid onset of laxative action (approximately 6-10 hours after ingestion instead of 2-3 days).

Accordingly, the present invention contemplates a method of treating constipation and constipation-related illness with a laxative effective amount of L-sugars such as L-fructose, L-mannose, L-sorbose, L-gulose and in particular, L-glucose. The present invention, therefore, contemplates a foodstuff, liquid, solid, pharmaceutical composition, crystal or powdered formulation administered in a dosage adjusted to provide the optimum laxative effective or laxative therapeutic response. For example, from about 6-12 grams of L-glucose once or twice per day can be administered to achieve satisfactory results in adults, i.e., for effecting increased bowel movement. A decided practical advantage is that the active compound may be administered in a convenient manner such as by oral administration. For calculations of dosage in units of g/kg (or mg/kg), a standard body weight of 70 kg is typically used for adult males. For women, a value of 58 kg body weight is used. For adolescents, small children and infants, weights of 40 kg, 20 kg, and 10 kg, respectively, are used. A therapeutic unit dosage range of 1 gram to about 3 grams of L-glucose can be recommended for softening the hardness of the stool. Overall, the preferred dosage of L-sugars can be in the range of about 1 gram to about 24 grams over a time period of 6-10 hours depending on the specific effect required and the age of the individual being treated. Effectiveness is a dose-response situation with lower doses exerting a milder (or stool softening) effect, and higher doses exerting a more intense laxative effect. The higher (e.g., 24 gram) dose (single dose 1-2× per day) can be used for those individuals requiring a more rapid or intense laxative effect.

The range of dosages for L-glucose are listed on the following table.

| Effectiveness of L-glucose | | | | |
|---|---|---|---|---|
| SUBPOPULATION | 1 g | 6 g | 12 g | 24 g |
| Adult Male | 15 mg/kg* | 86 | 171 | 343 |
| Adult Female | 17 | 103 | 207 | 414 |
| Adolescent | 25 | 150 | 300 | 600 |
| Child | 50 | 300 | 600 | 1200 |
| Infant | 100 | 600 | 1200 | 2400 |

*All dosages are in mg/kg of body weight.

The present invention contemplates liquid compositions with an effective amount of L-glucose, i.e., juices, sodas, syrups, or other types of digestible liquids and further contemplates solid compositions, such as powders or crystalline formulations.

L-glucose can be prepared in a solid formulation and employed in premeasured packets, e.g., 6 g/packet or in jars which can be measured with an enclosed scoop or a standard teaspoon. In the powdered form a rounded teaspoon of L-glucose is about 5 g and the crystal form is about 7.5 g. This dosage form can be mixed with juices, sodas, syrups, or other types of beverages in which it would add sweetness. The premeasured packets can also contain added flavor (e.g., cherry, strawberry, orange, etc.) and can be mixed with water to make a palatable laxative drink. Also, a premixed packet of L-glucose is contemplated with chocolate flavor for addition to milk. Further, a premixed packet of L-glucose can be added with semi-solid food for young children.

The juices contemplated herein can be fruit juices such as juice of orange, pear, apple, grapefruit, apricot, grape, lemon and mixtures thereof as well as reconstituted juices, i.e, juices concentrated by evaporating a significant amount of their water content and subsequently diluted to their usual strength by the addition of water. The juices herein can contain from 5% to 100% fruit juice. The sodas contemplated herein include clear carbonated beverages such as cola, cider-like soft drinks and ginger ale as well as carbonated beverages containing fruit juices. The syrups contemplated herein can include chocolate syrup and other flavored syrups, and caramel, corn or maple syrups.

The present invention also contemplates semi-solid compositions, containing laxative effective amounts of L-sugars, such as applesauces, unflavored and flavored puddings (e.g., chocolate, vanilla) and gelatin-based preparations specifically prepared for institutional use (i.e., hospitals and nursing homes).

The actual concentration of L-glucose in powdered or crystalline form would be adjusted to provide a final reconstituted concentration of 6 to 12 gms in 4 to 8 fluid ounces of beverage. Thus, concentrations would range from 0.025 gm/mL (6 gm/240 mL) to 0.1 gm/mL (12 gm/120 mL). For example, 12 g of L-glucose diluted in 240 ml of water administered to human subjects can produce negligible upper gastrointestinal tract symptoms, mild abdominal gas/flatus, and consistent and mild laxation within 24 hours by reports of diarrhea in 5 of 8 subjects, with most of these subjects reporting diarrhea within 12 hours. In addition, 80% of an oral dose of L-glucose is eliminated by the digestive tract (40% in stool, 20% in breath after colonic flora metabolism, 20% probably in flatus) and 20% is excreted in urine over a seven day period. After ingestion of 12 grams of L-glucose, the maximum urine excretion occurs in the first 6 hours; maximum stool excretion occurs in 6-12 hours and maximum breath excretion occurs 24-48 hours after dosing. These data illustrate that L-glucose induced-laxation results from malabsorption of the majority of ingested L-glucose.

The present invention contemplates foodstuffs, e.g. candy bars, wafers, containing L-glucose and other high intensity sweeteners to improve sweetener properties in a "food-type" matrix. These foodstuffs can typically contain from about 6 grams to about 12 grams of L-glucose per foodstuff. However, versatility is also an advantage in this form and many possibilities exist. Among these is a food or wafer matrix with 24 gm of L-sugar per about 30 grams to about 50 grams with perforations in the matrix to allow more accurate dosing. Other foodstuff formulations provide 6 grams to 12 grams of L-glucose per unit and are either individually wrapped or are packaged in a multi-use container. A 6 to 12 gram per unit formulation would allow titration of the stool softening or laxative dose to obtain a desired effect ("1 or 2 units as needed").

The present invention further contemplates pharmaceutical compositions including oral solutions or suspensions of L-sugars in a flavored base, or encapsulated tablets of L-sugars in a flavored base. This dosage form can contain, for example, a solution of from about 0.01 g to about 0.6 g of L-glucose per ml of solution. A liquid formulation of the invention can be prescribed as "one or two tablespoonfuls once or twice daily for constipation". The pharmaceutical compositions of the present invention can also be in the form of suppositories (e.g., cocoa butter, glycerin, or polyethylene-based).

The present invention also contemplates an enema solution utilizing L-sugars in a dosage form for laxative effective treatment such as a buffered solution containing from about 6 grams to about 12 grams of L-glucose per 120 mL of solution.

The following examples are given for purely illustrative purposes of this invention without limitation.

EXAMPLE 1

Study Design

When L-glucose was given to six human subjects in a preliminary study, mild gastrointestinal (GI) symptoms were present, including a laxative effect. Also, L-glucose was only partially recovered in urine and stool. Therefore, a more comprehensive study was designed to evaluate metabolism and elimination of L-glucose.

Eight healthy non-smoking males (22 to 31 yrs) with no previous history of GI illness were selected for the study. Meals (2230-2405 Kcal/day, 50% carbohydrate, 15% protein, 35% fat, 18-22 grams fiber/day) were provided to the subjects to insure constant dietary intake throughout the study. After seven days on the standard diets subjects fasted from midnight until 8:00 a.m. when they ate a light breakfast of toast and apple juice. Two hours later, they drank a solution of L-glucose (12 gm in 240 ml water) with 60 uCi of $^{14}C$ L-glucose. Subjects resumed their controlled diets 4 hours after ingestion of L-glucose and maintained the diets for the following 7 days.

Total urine and stool were collected at baseline and for the next 7 days. Blood samples were collected at designated time points for the first 24 hours. Breath $CO_2$ was sampled at the time of blood collection as well as once daily for the remaining 6 days. Subjects completed a questionnaire at various time points throughout the study to rate the intensity of physiological and GI symptoms including taste/aftertaste, nausea, stomach volume, hunger, abdominal pain, belching, bloating, gas/flatus, vomiting, and heartburn. Subjects also reported the number of stools and episodes of diarrhea (defined qualitatively as watery, loose, unformed or liquid stool) experienced each day. The quantitative clinical definition of diarrhea is stool weight which exceeds 200 gm/day.

Results

Physiological/gastrointestinal Effects

1. Taste/aftertaste

L-glucose was perceived by the subjects to have a pleasant taste with a mean score of 3.1 on a scale of 1 (pleasant) to 10 (unpleasant). Only one subject reported an aftertaste (scored as "5") for the L-glucose solution.

2. Gastric Volume and Hunger/Satiety

Figure 2:
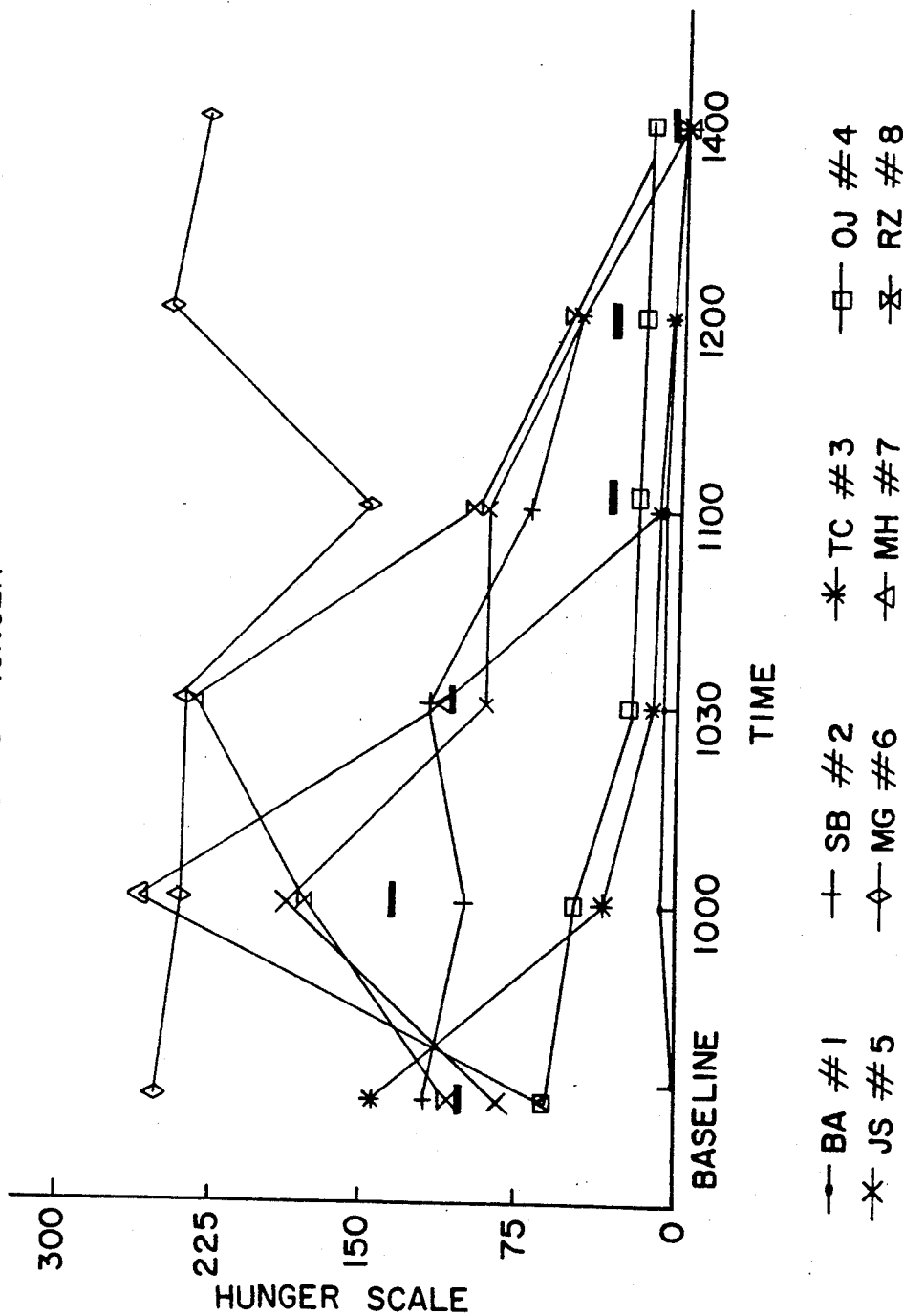
FIG. 2 is a graphical representation of the effect of L-glucose on the perception of hunger in human subjects.

As expected, the majority of subjects (5 out of 8) experienced an immediate increase in stomach fullness and were more sated after drinking the L-glucose solution (FIG. 1, FIG. 2). (Mean changes in perceived gastric volume are indicated by the black bars). Two subjects reported feeling less full immediately after ingestion of the L-glucose solution and one subject reported no change in stomach fullness.

3. Nausea

Figure 3:
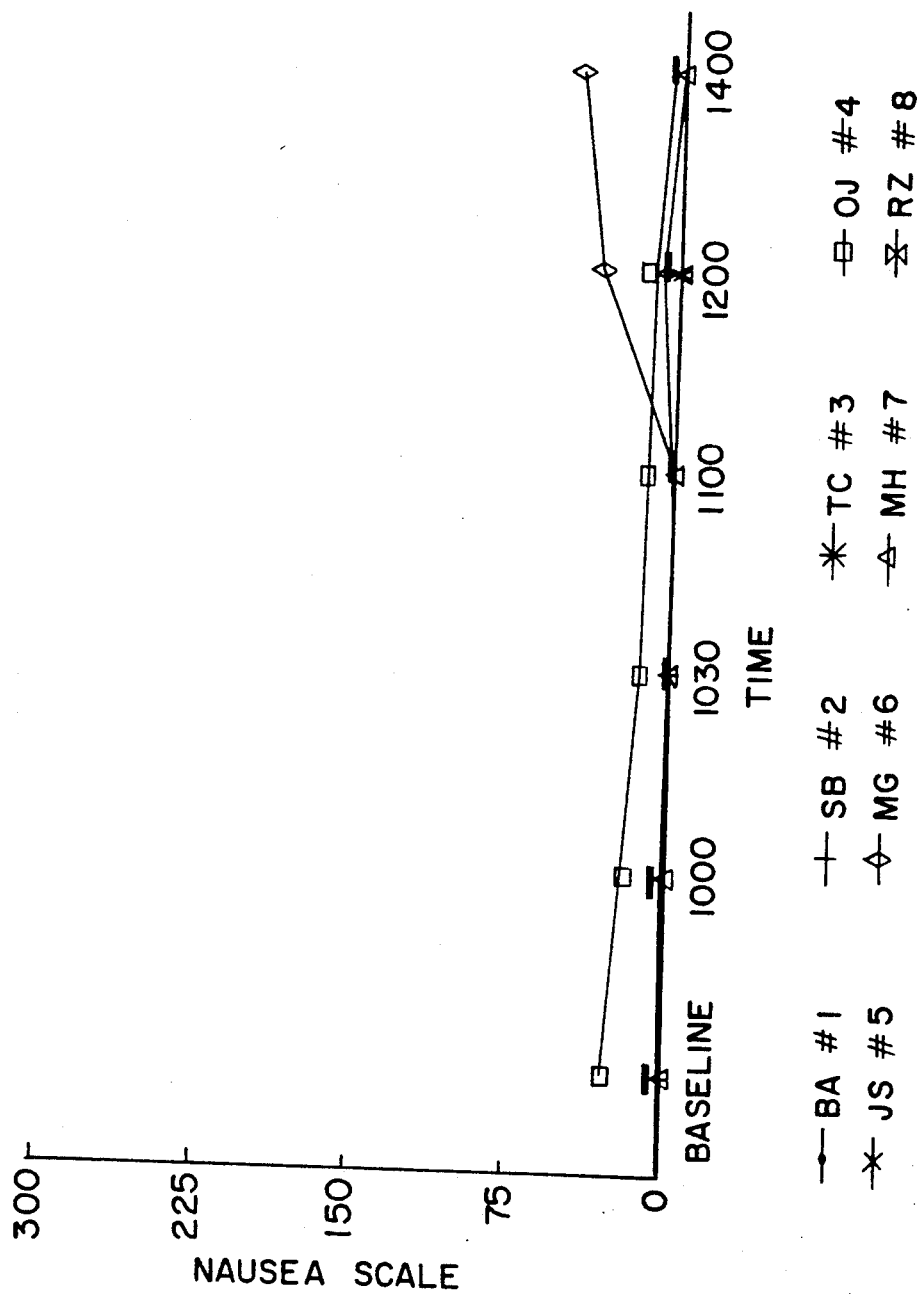
FIG. 3 is a graphical representation of the effect of L-glucose on nausea in human subjects.

The overall occurrence of nausea after ingestion of L-glucose was minimal to nonexistent (FIG. 3). One subject reported mild nausea both prior to and after drinking the test solution.

4. Belching

Figure 4:
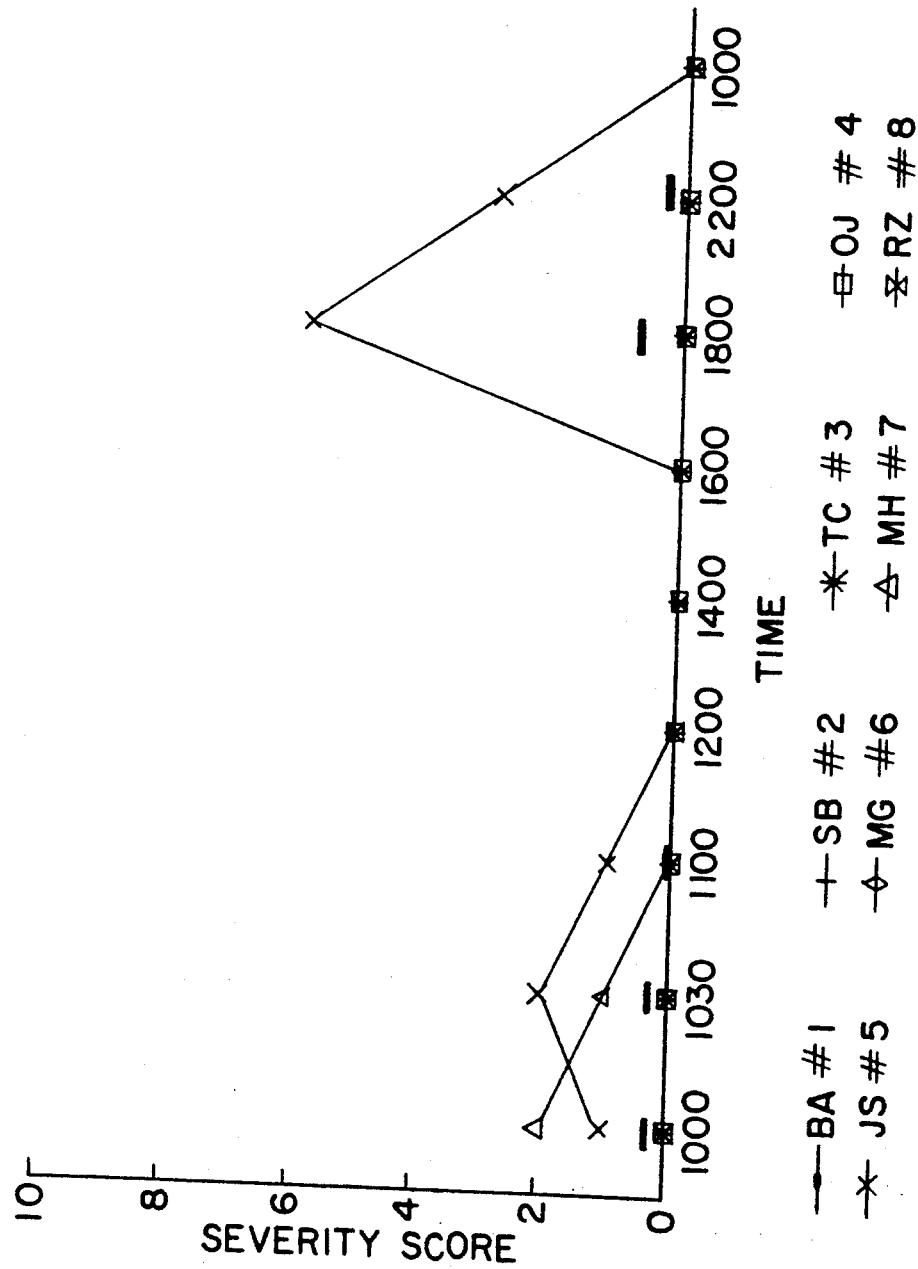
FIG. 4 is a graphical representation of the effect of L-glucose on belching/rifting in human subjects over a period of hours.
Figure 5:
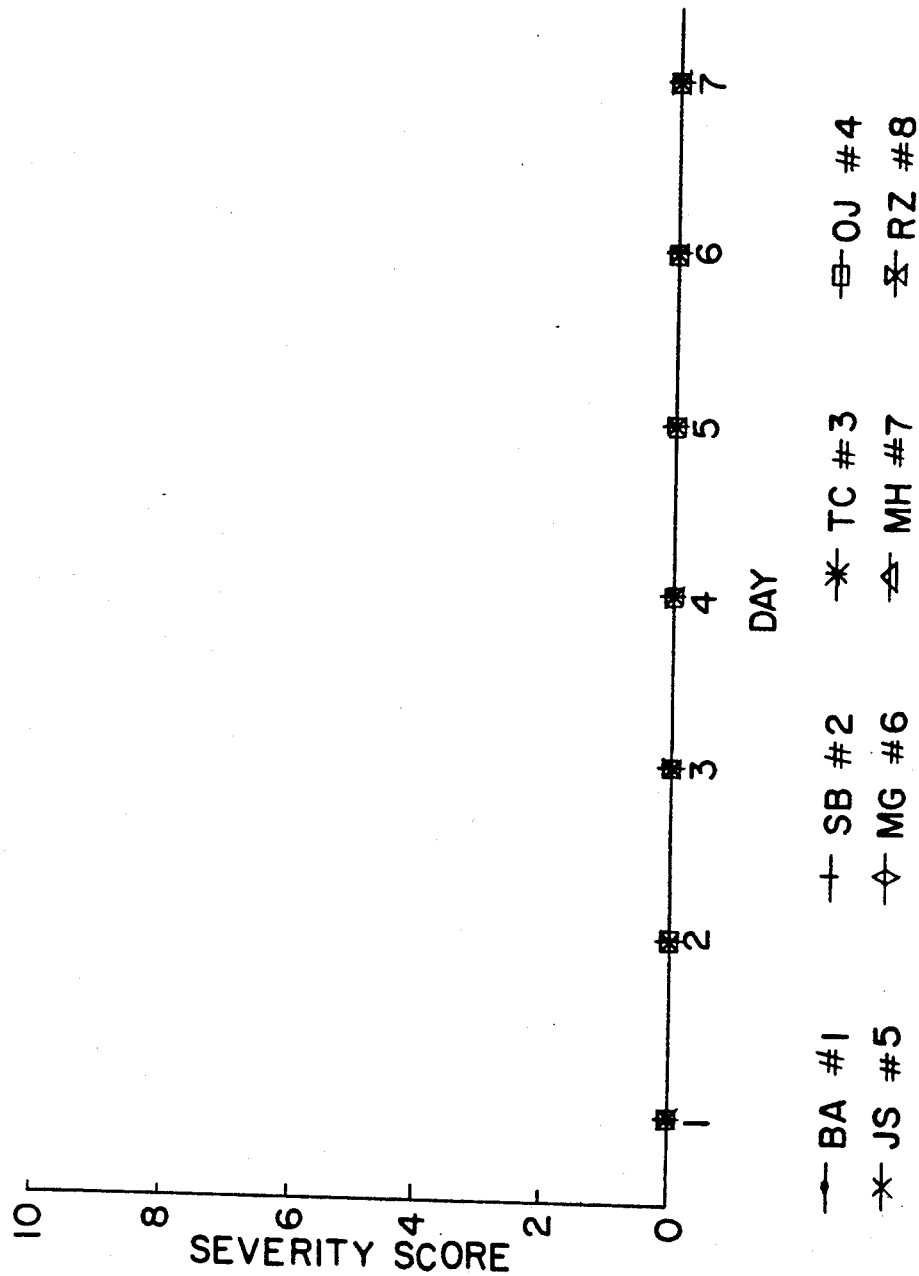
FIG. 5 is a graphical representation of the effect of L-glucose on belching/rifting in human subjects over a period of days.

Two of the eight subjects reported belching immediately after ingestion of L-glucose and rated the symptom "2" on a scale of 0 (none) to 10 (maximum/severe). One of these subjects reported increased belching eight hours after ingestion of L-glucose which also coincided with completion of his evening meal. No other reports of belching occurred on the remaining six days of the study (FIG. 4 and 5).

5. Gas/flatus

Figure 6:
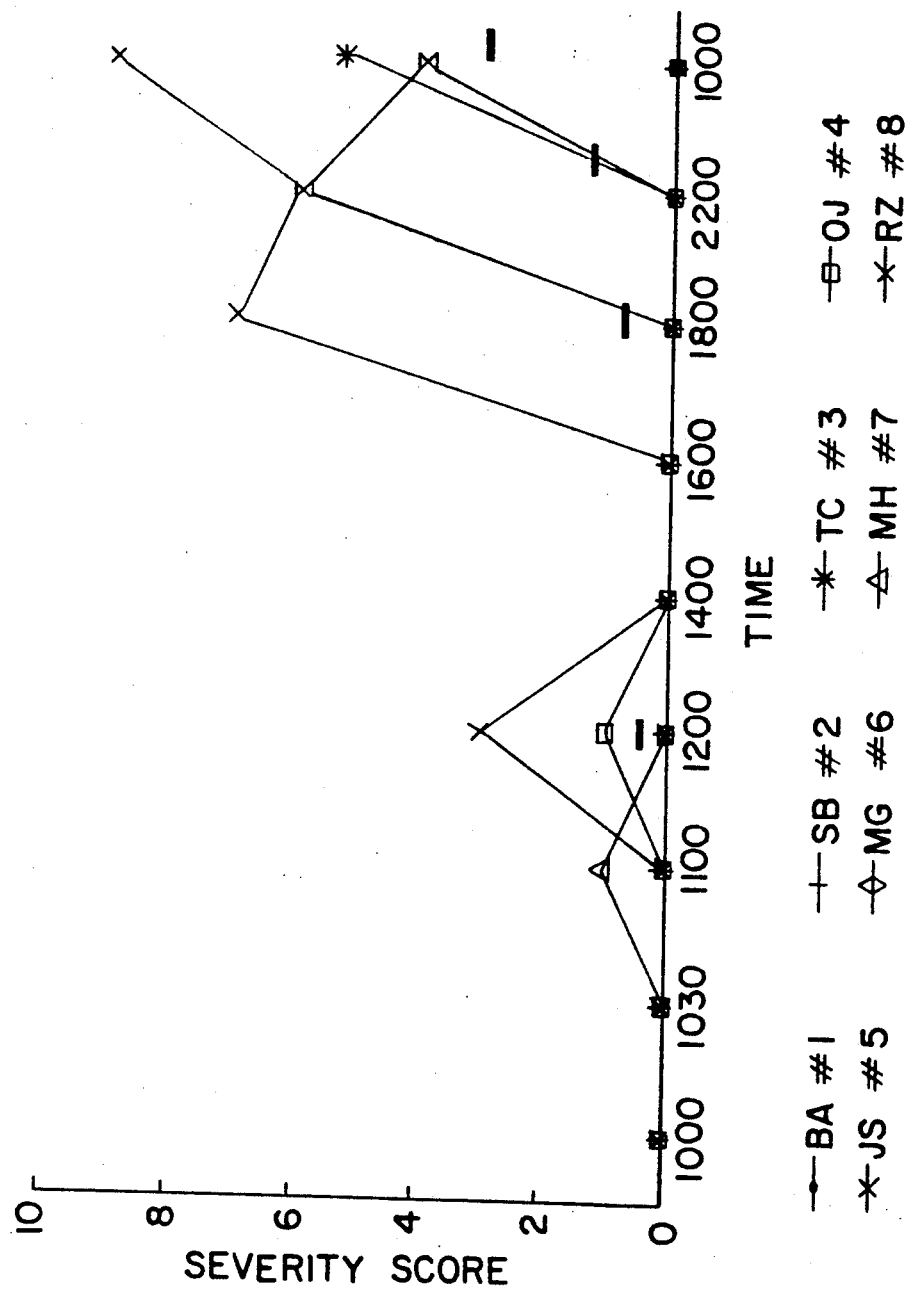
FIG. 6 is a graphical representation of the effect of L-glucose on gas/flatus in human subjects over a period of hours
Figure 7:
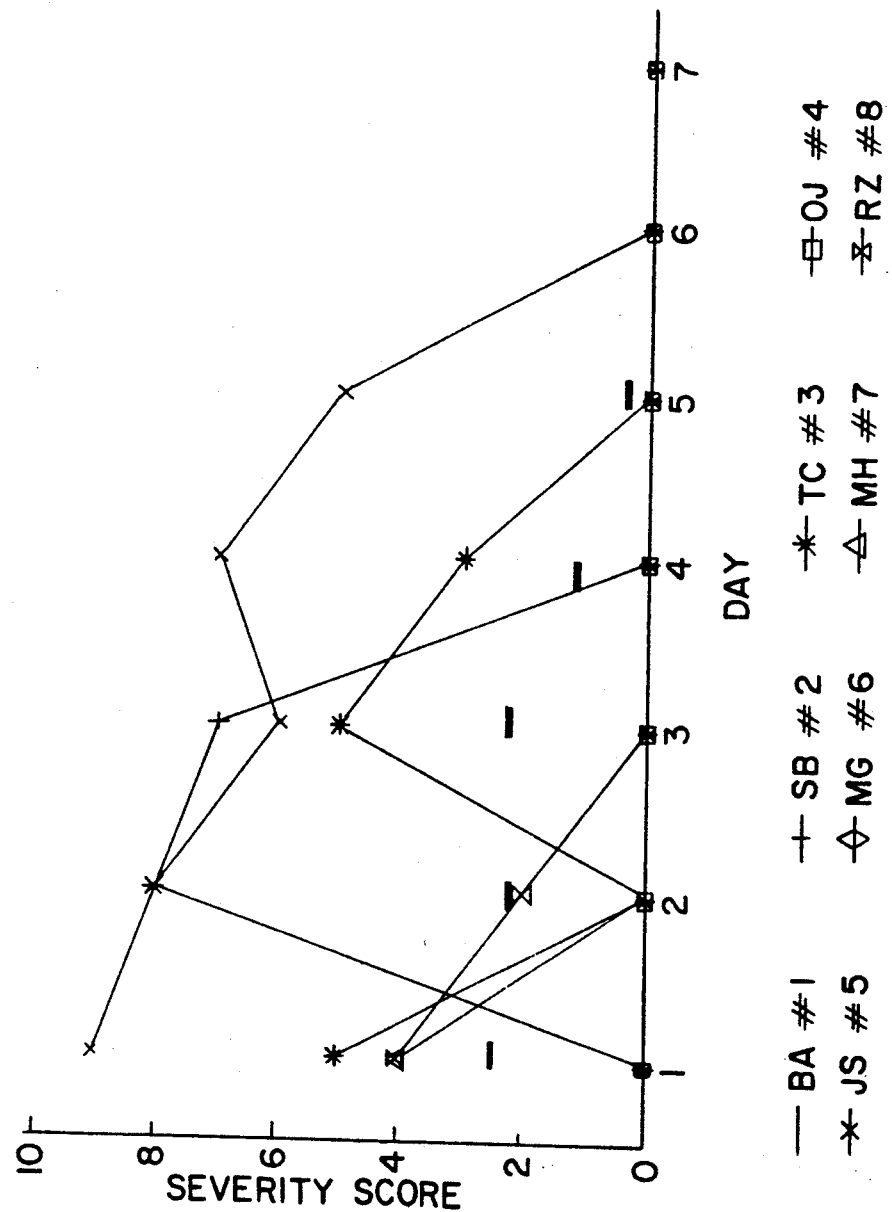
FIG. 7 is a graphical representation of the effect of L-glucose on gas/flatus in human subjects over a period of days.

Mild abdominal gas/flatus resulted after ingestion of L-glucose (FIG. 6 and 7). Four of eight subjects reported gas/flatus within 4 hours of drinking the L-glucose solution. By 12 hours after ingestion, five of the eight subjects reported some degree of flatulence ranging on the severity scale from 1 to 9; however, the mean score was 1.5, indicating that most of the subjects experienced only minimal levels of gas/flatus. At 24 hours, only three of the subjects reported flatus and one subject continued to report low levels of gas/flatus through day 5.

6. Diarrhea

Figure 8:
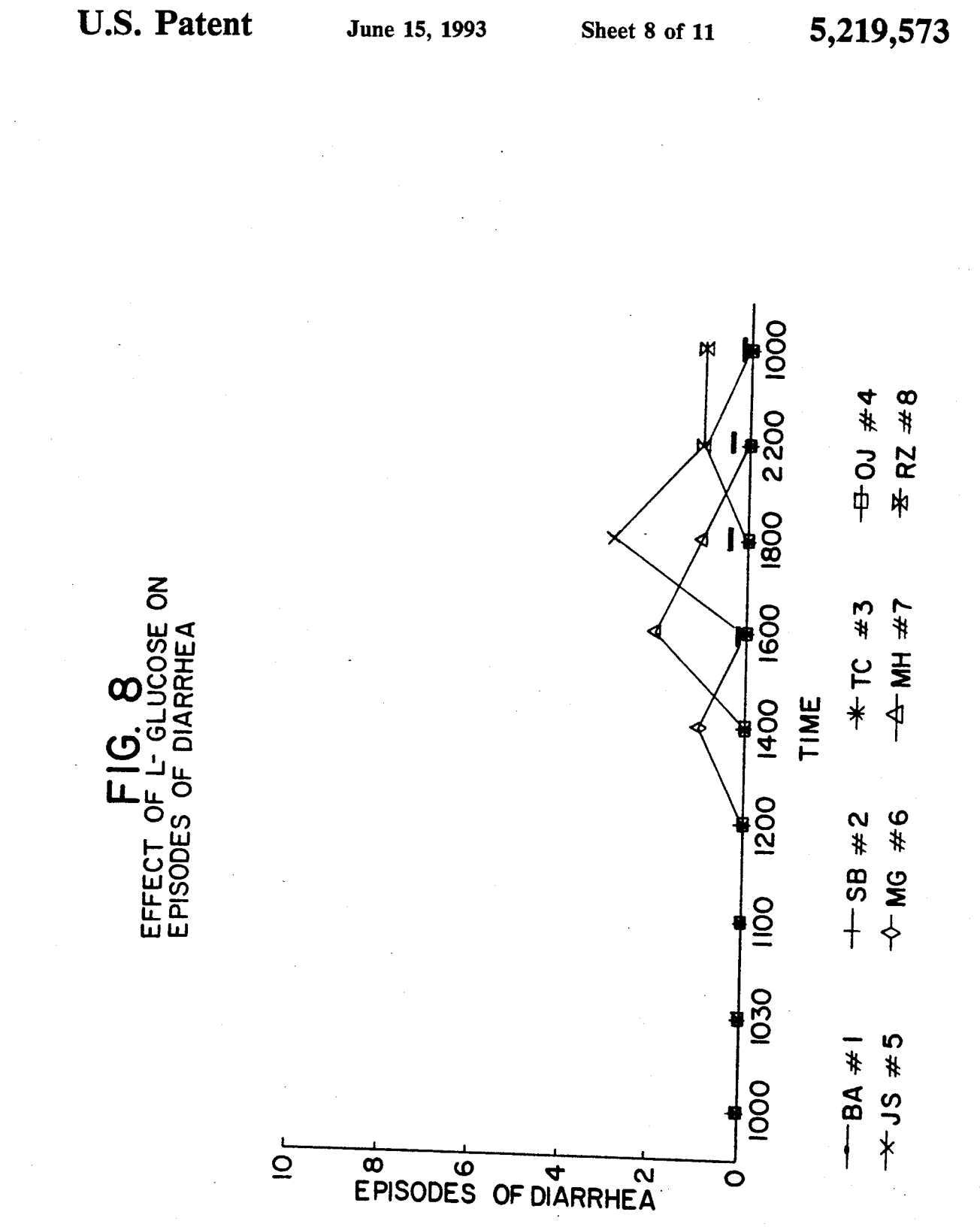
Figure 9:
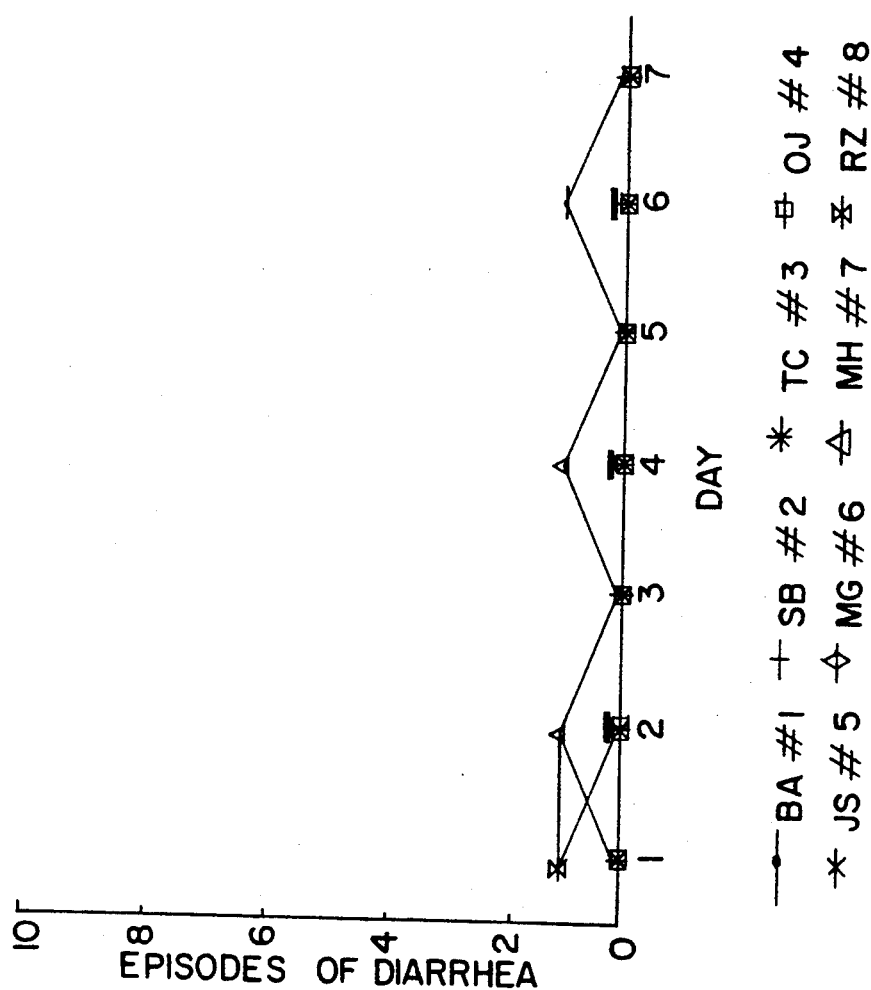
FIG. 9 is a graphical representation of the effect of L-glucose on episodes of diarrhea in human subjects over a period of days.

Consistent, mild laxation was indicated by reports of diarrhea in four of eight subjects within 12 hours of ingesting the L-glucose solution and five of eight subjects by 24 hours after ingestion of L-glucose (FIG. 8). Four of the eight subjects had quantitative diarrhea (greater than 200 gram/24 hour) by the end of day 1 (Table I). Sporadic occurrences of diarrhea were reported on days 2, 4, and 6 (FIG. 9).

Metabolism of L-Glucose

Results of this study indicated that approximately 43% of a radiolabelled ($^{14}C$) dose of L-glucose was recovered in the stool, 21% absorbed and excreted in the urine, and 17% expired as $CO_2$. The remaining 20% was not recovered and a portion of this possibly was passed as flatus. The total recovery of radiolabelled L-glucose averaged 81% from the eight subjects. Table II presents a summary of disposition of L-glucose in human subjects and Table III contains the individual data for the elimination of L-glucose from human subjects.

The intervals during which stool recoveries were the greatest were 2–6 hr (9%), 6–12 hrs (18%), and 24–48 hr (10%) after ingestion of L-glucose. Urine recovery of L-glucose was greatest in the first 24 hours after ingestion of the test solution. In contrast, the largest recoveries of radiolabelled $CO_2$ were during the time intervals of 12–24 hr (3%), 24–48 hr (8%), and 48–72 hr (5%).

EXAMPLE 2

In a subsequent study, seventy-five (75) healthy, non-smoking, nonmedicated male subjects were recruited. Screening questionnaires and medical histories were completed prior to study initiation to insure that the subjects had no history of gastrointestinal illnesses. Subjects were free-living and consumed their typical diets throughout the study.

Subjects were randomly assigned to three groups and received either L-glucose, sorbitol, or D-glucose in a food matrix. Following a normal breakfast at 7:00 a.m., the food product (containing 24 g of test compound) were ingested at approximately 10:00 a.m. consecutively for 3 days. Toleration was monitored by completion of a daily symptom record. This record allowed each subject to evaluate the degree of gastrointestinal (GI) effects including gas, bowel movements, stool characteristics, stomach fullness, cramps, and their interference with daily routine for the preceding 24 hours by use of the following six-point scale:

0 No change from normal range of experience
1 Barely noticeable change
2 Definitely noticeable but does not interfere with daily routine or activities
3 Barely interferes with daily routine or activities
4 Moderately intereferes with daily routine or activities
5 Seriously intereferes with daily routine or activities The laxative effect of these compounds were calculated using a separate scoring system based on stool frequency, characteristics, and urgency such that a score over 31 signified laxation.

Gastrointestinal Effects

Results of the subject evaluations are presented in Table 1 for the 24 hours after ingestion of the first food product in each group. Similar results were recorded for the second and third days of product ingestion.

Slight increases in abdominal cramps, nausea, and gas/flatus were noted by subjects who ingested food products containing L-glucose (Table 1). More dramatic increases in stool frequency and consistency were noted. Subjects who ingested the L-glucose product reported a mean of 5.3 stool episodes in 24 hours in comparison to 1.7 for subjects who ate the D-glucose products and 2.0 for those who ate the sorbitol product. A laxation score was also calculated from the number, consistency, urgency, and frequency of stools. The laxation score for L-glucose product was 48.0 while the laxation scores for D-glucose and sorbitol products were 3.6 and 7.9, respectively. L-glucose administered in the tested food matrix resulted in a definite increase in stool number, frequency, and urgency, and the consistency changed from normal to watery in most subjects.

EXAMPLE 3

In yet another study, eight healthy, non-smoking nonmedicated male subjects were recruited using the same criteria as in previous studies. Subjects were free-living and consumed their typical diets.

Subjects were asked to complete three-day trials in which they ingested a single solution of the following on day 2: 1) lactulose (12g/240 ml), 2) D-glucose (12g/240 ml), or 3) L-glucose (12 g/240 ml). Physiological and GI symptoms were monitored on all three days of each trial. On the evening of day 1 of each trial, subjects consumed a low carbohydrate meal and then refrained from food until 8 hours after consumption of the test solution. Test solutions were ingested the following morning between 7:00 and 10:00 a.m. Breath samples were collected before and at 30 minute intervals for eight hours after ingestion of the solution. Physiological effects were monitored simultaneously through a symptom questionnaire completed at each breath collection interval.

Breath samples were tested for hydrogen ($H_2$) concentration. A rise in breath $H_2$ concentration over baseline after ingestion of a test compound is indicative of malabsorption. Subjects were given lactulose during the first trial to verify that they possessed colonic bacteria capable of producing $H_2$ from a malabsorbed carbohydrate source.

Figure 10:
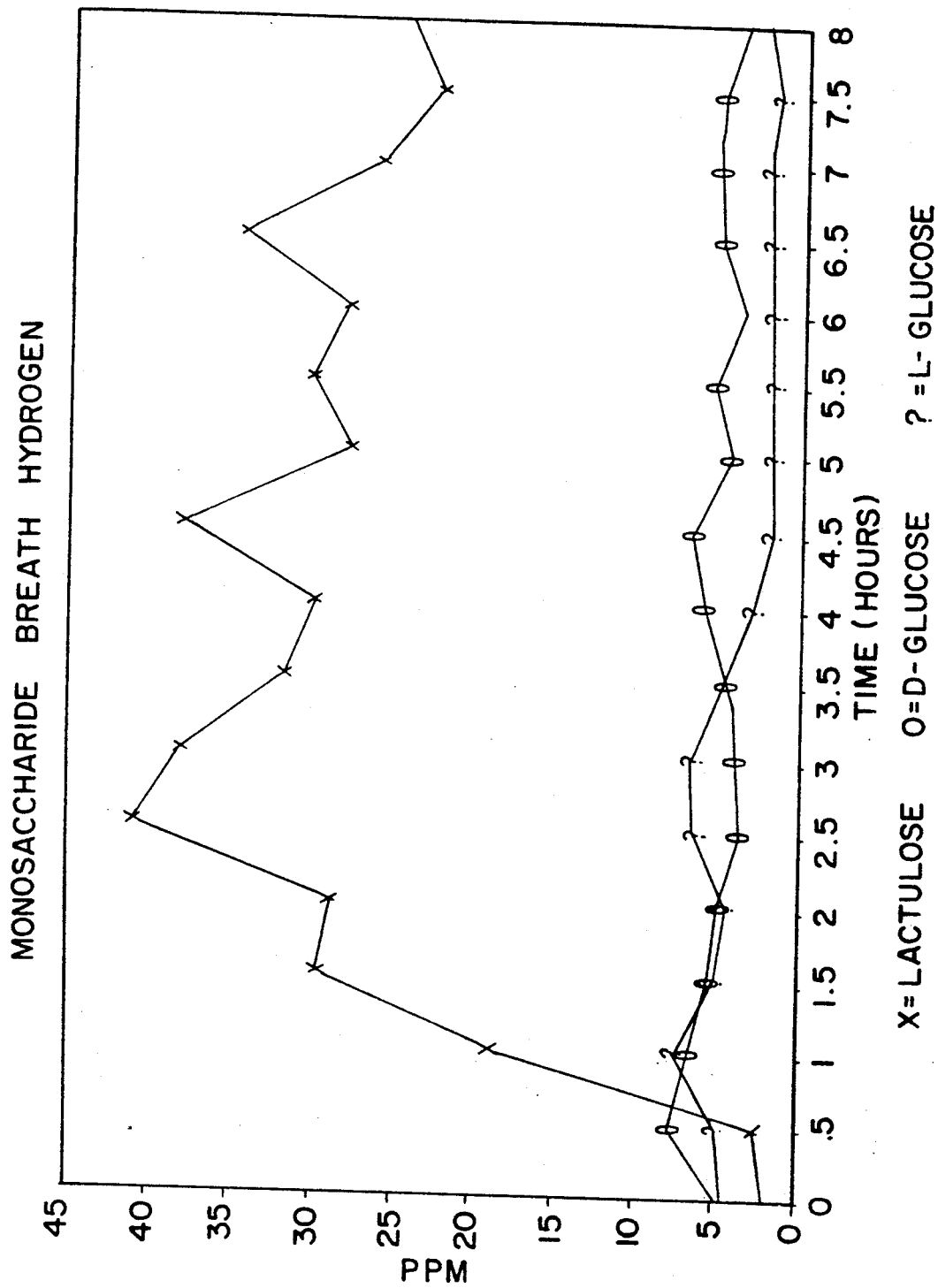
FIG. 10 is a graphical representation of the effect of L-glucose, lactulose, and D-glucose on breath hydrogen production in human subjects over a period of eight hours.

After ingestion of lactulose, all subjects showed a significant increase in breath hydrogen production. In comparison, subjects failed to produce breath hydrogen after ingestion of 12 grams of either D-glucose and L-glucose (FIG. 10). These results suggest that there was no bacterial degradation of L-glucose for at least the 8 hours immediately after ingestion during which breath hydrogen was monitored. This is a unique property for a malabsorbed sugar and may be a reason why L-glucose results in less flatus/gas than many conventional laxative agents such as lactulose.

L-glucose resulted in a laxation effect as indicated by laxation scores of 10.9 for L-glucose, 4.3 for lactulose, and 2.4 for D-glucose (FIG. 11). Subjects reported that L-glucose caused a substantial change in stool consistency and slight changes in stool frequency (time between stools) and number of stools/day.

EXAMPLE 4

The metabolism of several other L-sugars has been determined in the rat. Table 2 presents a metabolic summary for these sugars which include L-glucose, L-fructose, L-mannose, L-sorbose, and L-gulose. After administration of a single oral dose with radiolabel, 27-50% of L-mannose and 52-68% of L-gulose were excreted in the feces. These results indicate that these two compounds are not readily absorbed and therefore, are capable of exerting a laxative effect.

TABLE 1

| Symptom | D-glucose* | L-glucose* | Sorbitol* |
|---|---|---|---|
| Age | 27.9 | 27.8 | 28.3 |
| Height | 175.9 | 167.7 | 179.9 |
| Part I GI Effects | | | |
| Stomach fullness | 0 | 1.20 | 0.40 |
| Belching | 0.24 | 0.60 | 0.64 |
| Appetite | 0.04 | 1.28 | 0.08 |
| Abdominal cramps | 0.04 | 0.96 | 0.60 |
| Vomiting | 0 | 0.16 | 0 |
| Heartburn | 0.20 | 0.16 | 0.24 |
| Nausea | 0.04 | 0.84 | 0.08 |
| Gas/flatus | 0.40 | 1.44 | 1.44 |
| Frequency of stools | 0.20 | 3.44 | 0.48 |
| Consistency of stools | 0.04 | 3.44 | 1.08 |
| Other symptoms | 0.16 | 0.40 | 0.36 |
| Part II Laxation | | | |
| Number of stools | 1.68 | 5.28 | 2.00 |
| Consistency | 0.80 | 14.60 | 1.68 |
| Urgency | 0.36 | 18.72 | 2.52 |
| Frequency | 0.76 | 9.40 | 1.68 |
| Laxation score | 3.60 | 48.00 | 7.88 |

*Food product contained 24 g of test compound/dose.

TABLE 2

| COMPARATIVE METABOLISM OF SELECTED L-SUGARS | | | |
|---|---|---|---|
| | CO2 | URINE | FECES |
| | ORAL* | | |
| L-GLUCOSE | <2% | >95% | 4-8% |
| L-FRUCTOSE | 31-42% | 10-28% | 8-14% |
| L-MANNOSE | 35-38% | 7-11% | 27-50% |
| L-SORBOSE | 70% | 8-10% | 4-5% |
| L-GULOSE | 4-8% | 9-11% | 52-68% |
| | I.V.* | | |
| L-GLUCOSE | <0.2% | >96% | <1% |
| L-FRUCTOSE | — | — | — |
| L-MANNOSE | 1-2% | 88-91% | 1% |
| L-SORBOSE | — | — | — |
| L-GULOSE | 1-3% | 93-106% | 1-3% |

*PERCENT OF THE ADMINISTERED DOSE.

What is claimed is:

1. A method of providing stool bulking and laxation in mammals comprising orally administering a laxative effective amount of from about 6 to about 24 grams per day of a monosaccharide L-sugar.

2. The method according to claim 1 wherein the mammal is a human and is administered a laxative effective amount of from 86 mg per kg of body weight per day to 2400 mg per kg of body weight per day of a monosaccharide L-sugar.

3. The method according to claim 1 wherein said L-sugar is L-glucose.

4. The method of claim 1 wherein said effective amount is administered at least one a day.

5. A therapeutic composition for providing stool bulking and laxation comprising a laxative effective amount of rom about 0.01 g to about 0.6 g of L-monosaccharide sugar per ml and a pharmaceutically acceptable carrier.

6. The composition of claim 5 wherein said L-sugar is L-glucose.

7. A method of providing stool bulking and stool laxation in mammals comprising administering an amount of about 1 gram to about 12 grams per day of a monosaccharide L-sugar effective to achieve stool softening.

8. The method of claim 7 in which the amount of L-sugar ranges from about 1 gram to about 3 grams per day.

9. The method of claim 8 wherein the effective amounts are administered at least once a day.

* * * * *

UNITED STATES PATENT AND TRADEMARK OFFICE
CERTIFICATE OF CORRECTION

PATENT NO.   : 5,219,573
DATED        : June 15, 1993
INVENTOR(S)  : Stanley M. Tarka, et al.

It is certified that error appears in the above-indentified patent and that said Letters Patent is hereby corrected as shown below:

```
        On the Title Page,  Item    [56], before
"4,470,975" insert the following:
        --4,262,032  4/1981   Levin ...............426/658
          4,207,413  6/1980   Szarek, et al........536/1
          4,371,616  2/1983   Huibers..............435/101
          4,421,568 12/1983   Huibers..............127/48
          4,459,316  7/1984   Bakal................426/658 --
                     Item     [56], after "Canada"
on next line insert the following;
          --0091223  10/1983  United Kingdom--
        Column 3, line 58:  after "effect" insert --.--
        Column 12, line 54, Claim 5:  "rom"   should
read --from--
```

Signed and Sealed this

Twenty-fourth Day of May, 1994

Attest:

Attesting Officer

BRUCE LEHMAN

Commissioner of Patents and Trademarks